United States Patent

Sauer

[11] 4,007,494
[45] Feb. 15, 1977

[54] BONE CAP

[75] Inventor: Barry W. Sauer, Central, S.C.

[73] Assignee: Glasrock Products, Inc., Atlanta, Ga.

[22] Filed: Apr. 11, 1975

[21] Appl. No.: 567,237

[52] U.S. Cl. .................................. 3/1.9; 128/92 C
[51] Int. Cl.² .......................................... A61F 1/24
[58] Field of Search ...................... 3/1, 1.9–1.913; 128/92 C, 92 CA

[56] References Cited

UNITED STATES PATENTS

| 2,679,245 | 5/1954 | Timmermans | 128/92 CA |
| 3,314,420 | 4/1967 | Smith et al. | 128/92 C |
| 3,879,767 | 4/1975 | Stubstad | 3/1 |

FOREIGN PATENTS OR APPLICATIONS

| 1,046,920 | 7/1953 | France | 128/92 C |
| 1,107,877 | 8/1955 | France | 128/92 C |
| 764,600 | 12/1956 | United Kingdom | 128/92 CA |

OTHER PUBLICATIONS

Silastic Intramedullary Implant (Swanson Design), Dow Corning Pamphlet, Dow Corning Corp., Medical Products Division, Midland, Mich., Jan. 1969, pp. 1–9.
The Role of Porous Polymeric Materials in Prosthetic Attachment, author B. W. Sauer et al., presented at the Clemson University 5th Annual Biomaterial Symposium (Apr. 14–18, 1973) pp. 1–8.

*Primary Examiner*—Ronald L. Frinks
*Attorney, Agent, or Firm*—Lane, Aitken, Dunner & Ziems

[57] ABSTRACT

A cap for covering the exposed end of an excised bone including a head adapted to abut the exposed end. The outer surface of the head is free from sharp corners, at least the portion of the head adjacent to the exposed bone end being interspersed with a network of interconnected pores adapted for human tissue to grow therein and anchor the cap to the bone. The cap further includes means for preventing the pores from communicating with the outer surface of the head.

4 Claims, 3 Drawing Figures

BONE CAP

BACKGROUND OF THE INVENTION

This invention relates to a prosthetic device known as a "bone cap" and more specifically to a bone cap for children that is formed of a biocompatible material that is interspersed throughout by a network of interconnected pores.

Bone caps are prosthetic devices that are used to cover the exposed end of an excised bone. These devices have been used primarily in children under the age of sixteen in attempts to arrest a phenomenon known as "overgrowth." Overgrowth is a term used to describe a condition in children under the age of about sixteen where the exposed end of a bone that has been partially amputated continues to grow distally and form a pointed end.

Traditionally bone caps have been formed of a solid biocompatible material fixed in place by impacting a stem portion in the medullary canal or by applying sutures to holes formed in the device and in the adjacent portion of the bone. Although the bone cap may be tight initially, resorption usually occurs resulting in loosening of the device which then requires the cap to be fixed in place again.

SUMMARY OF THE INVENTION

The problem of arresting overgrowth has been solved by installing a bone cap that is formed substantially of a biocompatible material interspersed throughout by a network of interconnected pores of a predetermined size and at the same time is strong enough to withstand normal stress.

When the cap is fixed in place bone and other surrounding tissue will grow into the pores anchoring the cap firmly in place. The cap does not interfere with normal bone growth, but confines appositional growth of the end of the bone to the pores in the cap.

The phenomenon of continued tissue growth which operates to fill the pores also occurs in adults even though there is no overgrowth problem. Accordingly, such a bone cap could be used in adults, for example whenever the bone end must bear weight and is sensitive to pressure. In such a case the bone cap could serve as a cushion.

The cap should be shaped to cover the exposed bone end and have an outer surface that is free from sharp corners. The outer surface should also be covered with a solid coating of a biocompatible material so that the continued tissue growth is confined to the pores in the bone cap.

The cap includes either a stem that is inserted into the medullary canal or a cup or skirt portion that overlaps the bone along its length. Although both the stem and cup together are desirable to provide initial stability while tissue is growing into the pores, both of them are not essential in solving the overgrowth problem. The cap could be formed with either the cup or skirt alone and still provide the desired results.

Materials found to be particularly suitable for use in such bone caps are the recently development porous polymeric materials known as porous high density polyethylene and polypropylene or mixtures thereof. Porous high density polyethylene (porous HDPE) is preferred and offers considerable economic advantages. This material has been found to combine the features of (1) biocompatibility, (2) high enough strength to withstand normal stress to which bone caps are subjected, and (3) an interconnected cellular network that allows tissue ingrowth to occur throughout the cap. The following properties control the successful function of the bone cap:

1. density - between 0.945 and 1.965 g./cc. for porous HDPE and between 0.912 and 0.914 g./cc. for porous polypropylene,
2. molecular weight number - greater than 450,000 and up to over 6,000,000 depending on the availability of such material, which is the relative mass of a compound calculated in the basis of an atomic weight for oxygen of 16 and is derived by multiplying the atomic weight of each element of the compound by the number of atoms of that element in the compound and adding them all together,
3. melt index - between 0.005 and 5 (ASTM D1238-57T), which includes the combination of materials of different melt indexes within the above range, such as for example a blend of porous HDPE comprising 20% by weight of 0.960 density and 5 melt index and 80% of 0.960 density and 0.01 melt index,
4. average pore diameter - between 50 $\mu$m and 300 $\mu$m, as determined by the bubble technique (ASTME 128) or by the Aminco Micro/Macro Porosimeter distributed by the American Instrument Company, and varies according to the tissue, tendons and/or bone in which the prosthesis is to be used,
5. average pore volume - a minimum of 30% by weight, as determined by comparing the weight of the porous material with the weight of the material if it were not porous, which allows for proper random fixation (ingrowth) of the surrounding tissue without causing the device to fall below the minimum intrinsic strength needed to function properly.

Another significant characteristic of the material is called "tortuosity," which is a term used to describe the relationship of the interconnected pores to each other and means that for the most part there are no straight paths longer than the diameter of the largest pore. Furthermore, in order for the tissue to grow into the pores they should not have a diameter smaller than 50 $\mu$m and preferably about 100 $\mu$m. Although an average pore size of 50 $\mu$m would include some pores as small as 20–25 $\mu$m there would be enough larger pores to allow for some tissue ingrowth. The preferred minimum average pore size is about 75–80 $\mu$m which would encompass pores ranging from 45–50 $\mu$m in diameter to about 105–110 $\mu$m.

When the bone cap is formed of porous HDPE within the above parameters the material will be strong enough to withstand the normal wear and stress to which it will be subjected and at the same time allow the surrounding tissue to grow into the pores and anchor it firmly in place. Furthermore, the fact that the tissue can grow into the bone cap to the extent allowed by being porous throughout prevents the cap from lossening because of the overgrowth problem mentioned above and arrests overgrowth by allowing bone tissue to grow into the pores instead of between the bone and the cap.

BRIEF DESCRIPTION OF THE DRAWING

For a better understanding of the invention, reference may be had to the following description of an exemplary embodiment, taken in conjunction with the accompanying drawing, in which.

DETAILED DESCRIPTION OF AN EXEMPLARY EMBODIMENT

Figure 1:
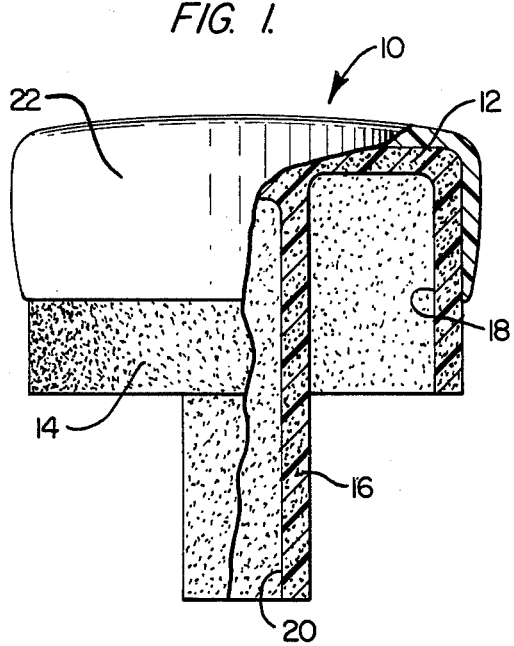
FIG. 1 is a side view, partially in section, of the inventive bone cap.
Figure 2:
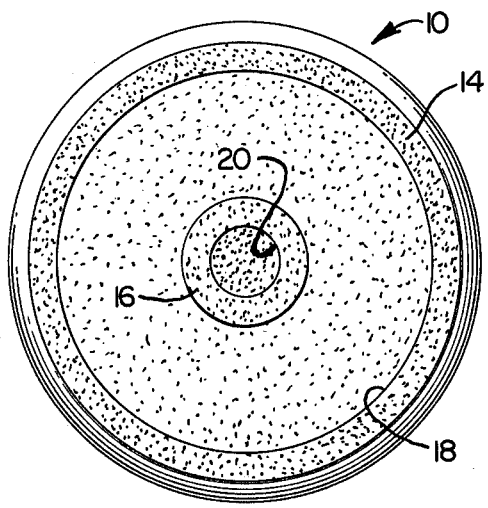
FIG. 2 is a bottom view of the bone cap shown in FIG. 1.
Figure 3:
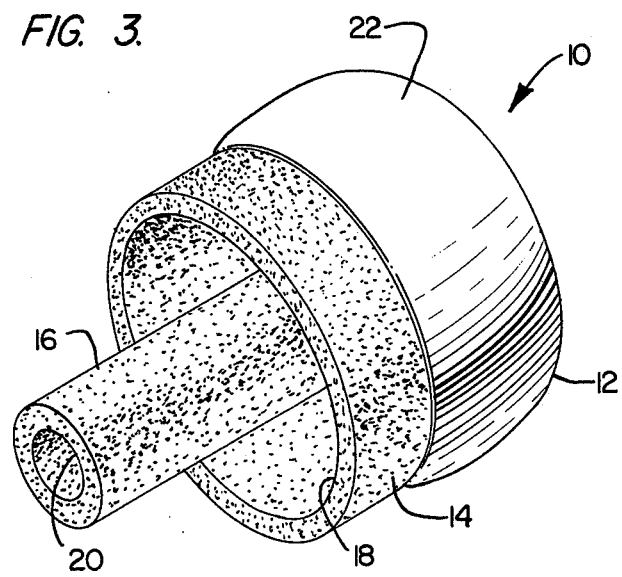
FIG. 3 is a perspective view of the bone cap shown in FIGS. 1 and 2.

Now, referring to the drawing, the bone cap is shown generally by reference numeral 10. The bone cap 10 includes a rounded head 12 and a cup or skirt 14 projecting axially from the head 12. A stem 16 also projects from the head 12 and is coaxial with the skirt 14, forming a cylindrical opening 18 therebetween. An axial opening 20 extends through the stem 16 and terminates at a suitable point therein.

The bone cap is sized and shaped such that when the stem 16 is inserted into the medullary canal (not shown) of a partially amputated bone the skirt 14 will overlap the outer surface of the bone and the bone will fill the opening 18. The outer surface of the head 12 is rounded so that it contains no sharp angles or corners that could irritate surrounding tissue.

The cap could alternatively be formed with either the skirt 14 or stem 16 alone. However, when both are provided there is added stability while the bone is growing into the pores.

The axial opening 20 is likewise not necessary for a satisfactory bone cap, but can be included to provide another porous surface into which tissue can grow and to enable blood vessels in the medullary canal to have more direct access to tissue in the pores.

The outer surface of the head 12 above the end of the bone is covered by a non-porous coating 22 of a biocompatible material to restrict the extra tissue growth to the pores. Any suitable material such as polyethylene, polypropylene or silicone rubber could be used for the coating. One method of forming such a coating is known as "spin-welding" which is a term used to describe the process of simultaneously spinning the cap and applying heat thereto. It has been found that for porous HDPE the material on the outer surface of the head 12 will melt and fuse together to form the necessary non-porous coating 22.

As discussed in detail above, the bone cap 10 can be formed of porous HDPE or porous polypropylene but any other material that includes (1) the interconnected network of pores, (2) biocompatability, and (3) the necessary strength characteristics, can be used.

Although it is desirable to form the bone cap entirely of the porous material (except for the coating 22) it can have a composite structure with a solid core that has an outer coating of the porous material. When such a structure is used, the porous coating should be at least 1 mm. thick and preferably 2-3 mm. thick to allow for enough tissue ingrowth to anchor the cap.

Thus, there is provided a novel bone cap for children that does not become loosened. Moreover, the cap becomes anchored in place without the need for any additional means of attachment. The embodiment of the invention described in detail above is intended merely to be exemplary and those skilled in the art will be able to make modifications and variations to it without departing from the spirit and scope of the claims appended hereto.

I claim:

1. An improved cap for covering the stump of a partially amputated bone, and preventing bone overgrowth in juveniles, comprising a head adapted to abut and overlap the end of the stump, the outer surface of the head being free from sharp corners, at least the portion of the head adjacent to said end of the stump with a thickness of at least 1 mm. being formed of a porous polymeric material with a density of at least 0.912 g./c.c. interspersed with a network throughout its volume of interconnected pores with no straight paths longer than the diameter of the largest pore and adapted for human tissue to grow therein, said porous polymeric material having an average pore diameter ranging from 50 $\mu$m – 300 $\mu$m, the minimum pore volume being 30%, a non-porous cover on the portion of the outer surface of the head which projects beyond the end of the stump for preventing the pores from communicating with said portion of the outer surface.

2. The cap in claim 1, wherein the head includes a stem projecting from the side thereof adapted to abut said exposed end.

3. The cap in claim 2, wherein the stem includes an axial opening therein.

4. The cap in claim 1, wherein the cap is formed substantially entirely of porous HDPE.

* * * * *

UNITED STATES PATENT OFFICE
CERTIFICATE OF CORRECTION

Patent No. 4,007,494    Dated February 15, 1977

Inventor(s) BARRY W. SAUER

It is certified that error appears in the above-identified patent and that said Letters Patent are hereby corrected as shown below:

Column 2, line 6, after "and" "1.965" should read -- 0.965 --.

Signed and Sealed this

Third Day of May 1977

[SEAL]

Attest:

RUTH C. MASON
Attesting Officer

C. MARSHALL DANN
Commissioner of Patents and Trademarks